United States Patent [19]

Singh

[11] Patent Number: 4,785,795

[45] Date of Patent: Nov. 22, 1988

[54] HIGH-FREQUENCY INTRA-ARTERIAL CARDIAC SUPPORT SYSTEM

[75] Inventor: Param I. Singh, Lexington, Mass.

[73] Assignee: Abiomed Cardiovascular, Inc., Danvers, Mass.

[21] Appl. No.: 8,061

[22] Filed: Jan. 14, 1987

Related U.S. Application Data

[63] Continuation of Ser. No. 755,107, Jul. 15, 1985, abandoned.

[51] Int. Cl.⁴ .............................................. A61B 19/00
[52] U.S. Cl. ...................................... 600/18; 604/101
[58] Field of Search ................. 128/1 D, 207.15, 325, 128/344; 604/23, 49, 52, 53, 67, 96–103, 120, 151

[56] References Cited

U.S. PATENT DOCUMENTS

| | | | |
|---|---|---|---|
| 2,854,983 | 10/1958 | Buskin | 604/96 |
| 3,592,184 | 7/1971 | Watkins et al. | 128/1 D |
| 3,709,227 | 1/1973 | Hayward | 128/207.15 |
| 3,939,820 | 2/1976 | Grayzel | 128/1 D |
| 4,077,394 | 3/1978 | McCurdy | 128/1 D |
| 4,154,227 | 5/1979 | Krause et al. | 128/1 D |
| 4,329,993 | 5/1982 | Lieber et al. | 604/98 |
| 4,407,271 | 10/1983 | Schiff | 128/1 D |
| 4,423,725 | 1/1984 | Baran et al. | 604/101 |
| 4,531,936 | 7/1985 | Gordon | 604/52 |
| 4,546,759 | 10/1985 | Solar | 128/1 D |

Primary Examiner—John D. Yasko
Assistant Examiner—Mario Costantino
Attorney, Agent, or Firm—Lahive & Cockfield

[57] ABSTRACT

Disclosed is a high-frequency intra-arterial cardiac support system having a balloon pump which may be positioned in a major artery downstream of a natural heart. The balloon pump comprises a pumping balloon of small displacement mounted upon and cyclically inflatable and deflatable by fluid flow through catheter having a lumen leading to the outside of the body. The balloon pump further comprises a valve mounted downstream of the pumping balloon. The system further comprises a control and drive mechanism for providing cyclical fluid flow to the lumen of the catheter for inflation and deflation of the pumping balloon. The cyclical flow and the cyclical inflation and deflation occur at a frequency which is at least three times the normal beating frequency of the natural heart. The small displacement of the pumping balloon is much smaller than the normal stroke volume of the natural heart.

12 Claims, 3 Drawing Sheets

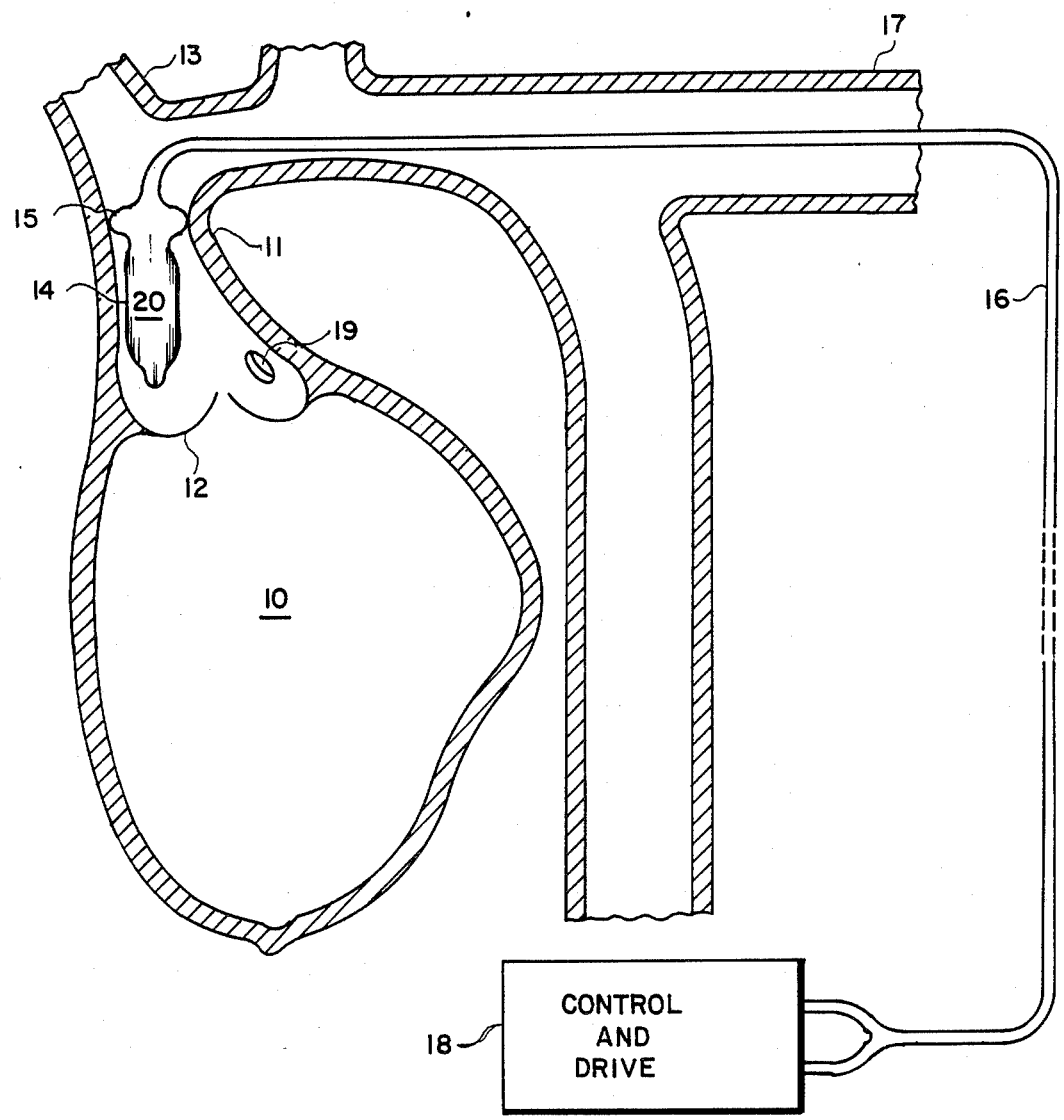
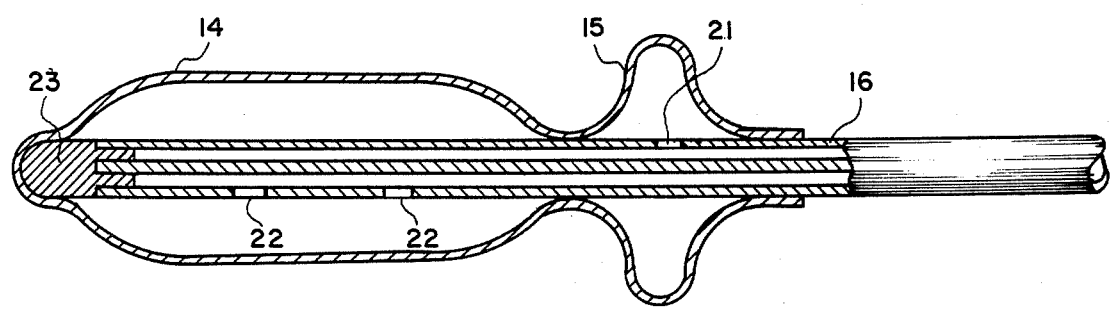

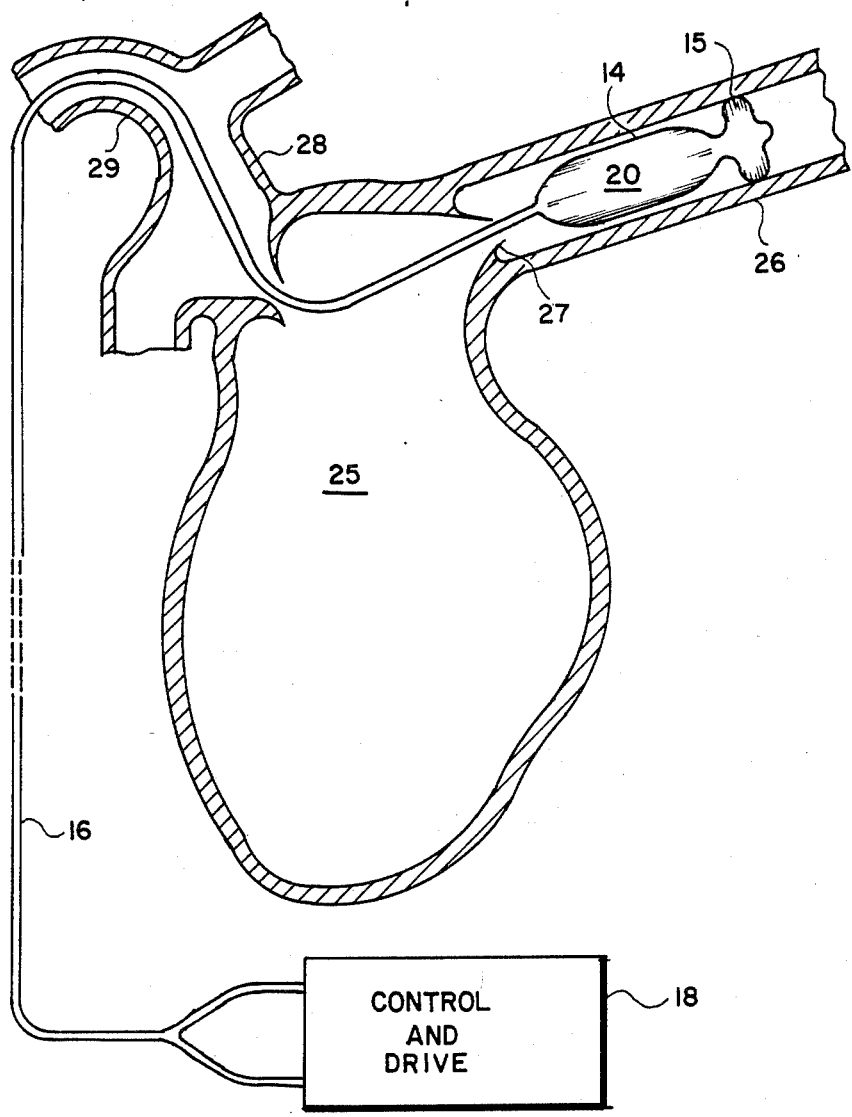
_Fig 3_
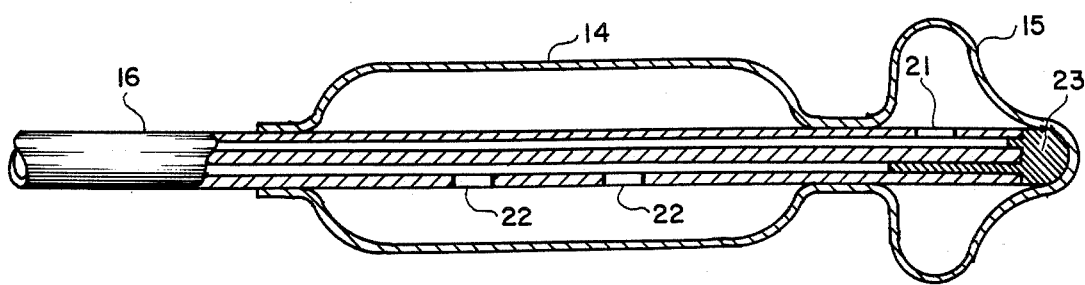
_Fig 4_

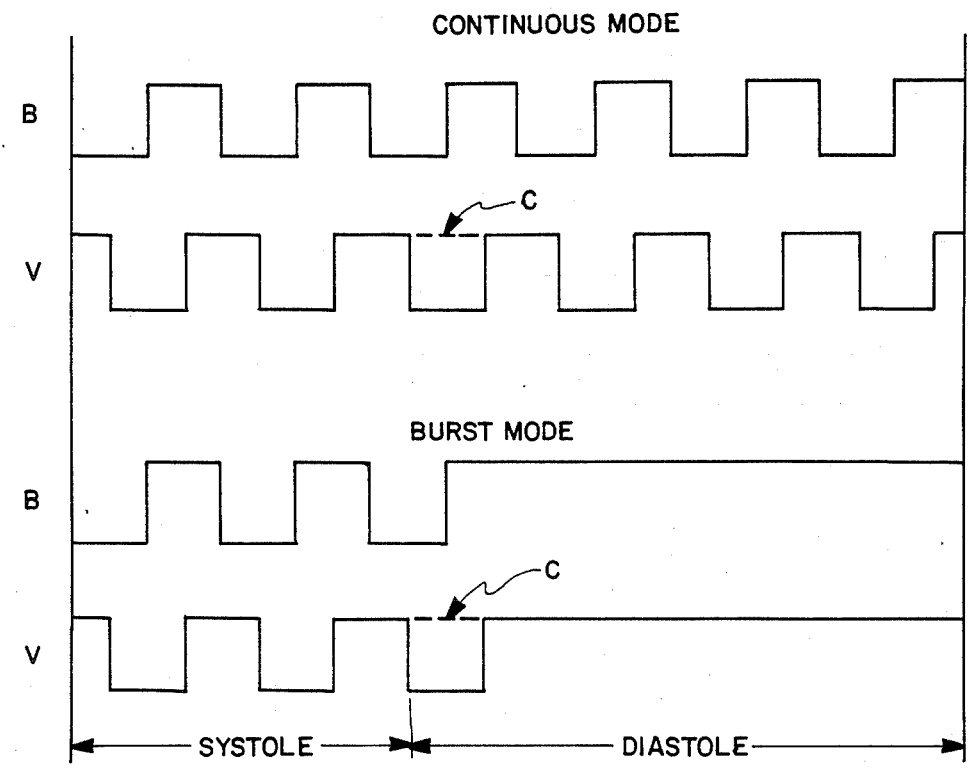
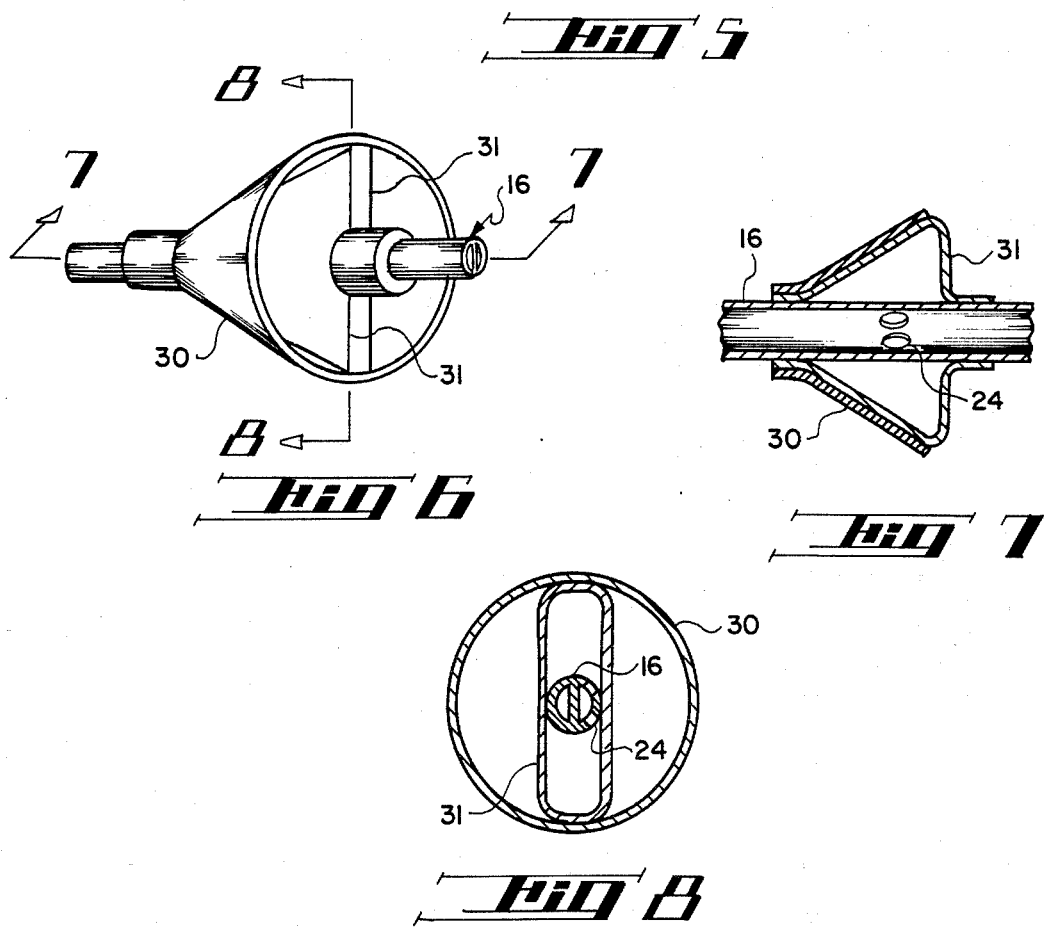

HIGH-FREQUENCY INTRA-ARTERIAL CARDIAC SUPPORT SYSTEM

This application is a continuation of application Ser. No. 755,107, filed July 15, 1985, now abandoned.

BACKGROUND OF THE INVENTION

1. Field of the Invention

This invention relates generally to temporary cardiac assist devices used to assist the operation of a failing, traumatized or infarcted heart for a limited period until either the heart recovers or more definitive treatment can be provided. In particular, it relates to so-called intra-aortic balloon pumps. Such a pump does not require major thoracic surgery to connect it to the circulation but is a collapsible structure which may be introduced into an easily accessible large artery, such as a femoral, and may then be guided into some portion of the aorta, usually the thoracic aorta, where it can be employed to assist the left side of the heart, the side most frequently in need of assistance and the driving force behind the systemic circulation. In the usual "counterpulsation" mode of employment, the balloon is pneumatically inflated during diastole to increase blood pressure and deflated during systole to lower the pressure load upon the ventricle. This device and its mode of operation was described in a paper by Moulopolous, Topaz and Kolff, "Diastolic Balloon Pumping in the Aorta—A Mechanical Assistance to the Failing Circulation", American Heart Journal (1962) 63, p. 669.

2. Prior Art Problem

Since intra-aortic balloon pumps can be applied with relatively minor surgery and fairly standard vascular catheterization procedures, and afford some useful assistance to the left heart, they are well regarded. However, they provide much less pumping assistance than one would desire, for at least three reasons: first, the conveniently available volume within the aorta is not large compared to the desired stroke volume of the heart; second, the necessity to avoid occlusion of important arteries such as the carotids and renals, and erosion of atherosclerotic plaques, further limits the size of a pump balloon; and third, the elastic compliance of the aortic walls makes the effective pumping displacement of the balloon less than its geometric displacement. Many inventions have been addressed to the alleviation of this problem: For example, U.S. Pat. No. 3,504,662 to R. T. Jones shows how to attain better pump fluid dynamics, and U.S. Pat. No. 3,692,018 to Goetz and Goetz shows how to direct the limited available flow predominantly to the critical brain and heart circulations. Still, there is no complete solution to the problem of adequate pump output. Also, since the counterpulsation mode requires synchronization with the natural heart, there is a further problem when the available ECG signal is weak, uneven or missing, as may occur in ill patients.

SUMMARY OF THE INVENTION

It is therefore the principal object of this invention to provide an intra-arterial cardiac support system which can fully support the left heart by pumping the entire stroke volume of the heart while maintaining a low systolic intraventricular pressure. It is a further object of this invention to provide such full support with a balloon pump structure which is physically small, as required for easy insertion and safe operation. Further objects of this invention are to provide means for similar support to the right and to provide means for supporting circulation even when the heart is atonic or fibrillating.

According to this invention, the desired objects are attained by positioning a small balloon pump, provided with valve means on its downstream side, in a major artery immediately adjacent to the heart, such as in the ascending aorta between the aortic valve and the ostium of the innominate artery, or in the pulmonary trunk. This small balloon pump is cyclically inflated and deflated at a frequency much higher than that of the beating of the heart, whereby the ejected stroke volume of the ventricle is pumped away by several rapid cycles of balloon pumping. Other objects of this invention, as well as the means for attaining them, are set forth in the accompanying Specification and Drawings, wherein:

BRIEF DESCRIPTION OF THE DRAWINGS

FIG. 1 is a schematic view of the high-frequency intra-arterial cardiac support system in its mode of employment in support of the left heart.

FIG. 2 is a cross-section view of a preferred embodiment of the balloon pump of this invention as used in the mode of employment illustrated in FIG. 1.

FIG. 3 is a schematic view of the high-frequency intra-arterial cardiac support system in its mode of employment in support of the right heart.

FIG. 4 is a cross-section view of a preferred embodiment of the balloon pump of this invention as used in the mode of employment illustrated in FIG. 3.

FIG. 5 is a timing diagram illustrating the sequences of inflation and deflation of the parts of the preferred embodiment of the balloon pump.

FIG. 6 is a perspective view of an alternative form of the valve part of the balloon pump.

FIG. 7 is a sagittal cross-section of the valve shown in FIG. 6, in the plane indicated by 7—7 in that Figure.

FIG. 8 is a normal cross-section of the valve shown in FIG. 6, in the plane indicated by 8—8 in that Figure.

DESCRIPTION OF THE INVENTION

Reference is made to FIG. 1, which is a schematic view of the high-frequency intra-arterial cardiac support system in its mode of employment in support of the left heart. Left ventricle 10 is assisted by balloon pump 20 located in ascending aorta 11 between aortic valve 12 and the ostium of innominate artery 13. Pump 20 comprises pumping balloon 14 and valve 15 downstream from balloon 14, both attached to two-lumen catheter 16 which is brought outside the body through the arterial tree, as via subclavian artery 17 in the Figure.

Pump 20, as seen more particularly in FIG. 2, comprises a shaped hollow tubular body of thin elastomeric material cemented to two-lumen catheter 16 to form pumping balloon 14 and valve 15. The end of catheter 16 is closed, and the end of balloon 14 is supported, by closure 23, which may advantageously be made of radio-opaque material to facilitate placement of the device. The interior of pumping balloon 14 is connected fluidically to one lumen of catheter 16 by holes 22, and the interior of valve 15 is connected fluidically to the other lumen by hole 21. In the Drawings, dimensions such as thicknesses have been exaggerated in the interest of clarity.

Referring again to FIG. 1, it is seen that the outside diameter of valve 15, when erected by inflation, should be just sufficient to substantially occlude ascending aorta 11, and the outside diameter of pumping balloon 14 should be somewhat less. Clearly, a number of sizes will be needed to fit the population of potential patients. In most adults, the inside diameter of the ascending aorta is of the order of of 2.5 centimeters, and the available length for the balloon pump, between the aortic valve and the ostium of the innominate artery, is of the order of 5.0 centimeters.

It can also be seen that two-lumen catheter 16 is connected to control and drive mechanism 18 which cyclically and individually inflates and deflates balloon 14 and erects and collapses valve 15 by fluid flow through lumens of catheter 16. The elements of such mechanisms are well known in the art, but the operating parameters of the mechanism of this invention are quite unusual. In particular, the frequencies of inflation and deflation are much higher, and the inflation and deflation volumes are much lower, than those of prior art devices, as will be set forth in greater detail hereinbelow.

Reference is now made to FIG. 3, which is a schematic view of the high-frequency intra-arterial cardiac support system of this invention in its mode of employment in support of the right heart. Here, right ventricle 25 is assisted by balloon pump 20 located in pulmonary trunk 26 just downstream from pulmonary valve 27. In this application, it is preferable that the catheter be placed in the venous system, leading out through right ventricle 25 and superior vena cava 28 and a brachiocephalic vein 29. It will be noted that valve 15 is again located downstream from pumping balloon 14, but that the different direction of approach of the catheter requires that the valve now be placed at the far end of the assembly. This arrangement is shown in detail in FIG. 4, where similar numbers refer to similar elements in the arrangement shown in FIG. 2.

Reference is now made to FIG. 5, which is a timing diagram illustrating the sequence of inflations and deflations of the pumping balloon and the valve of the preferred embodiment of the balloon pump of this invention. Two modes of operation are shown, called respectively "continuous" and "burst". In each case, the letter "B" refers to the pumping balloon and the letter "V" refers to the valve. Upward displacement of a trace signifies increased pressure, or inflation, and downward displacement signifies decreased pressure, or deflation. It will be recognized that the waveforms shown are illustrative only of timing relationships, and that actual balloon and valve pressure and flow waveforms will be quite rounded, approaching the sinusoidal for high frequencies of inflation and deflation.

Examination of the solid-line "continuous mode" traces of FIG. 5, in the context of the arrangements shown in FIGS. 1 and 3, shows that in each case the phasing of the motions of the pumping balloon and the valve, in the presence of the natural valves of the heart, is such as to cause peristaltic pumping of the blood away from the natural valves, and in the direction of natural flow. Considerations of desired pumping throughout and available space for the balloon pump indicate that the balloon pump should make at least three pumping cycles for each beat of the heart, and preferably more, in order to permit a smaller and more easily inserted and positioned balloon pump. This leads to the rule of thumb that the pumping frequency of the balloon pump must be at least three times the beating frequency of the heart.

If it is desired to unload the natural ventricle completely, one may employ the "burst mode" illustrated in FIG. 5, in which all the pumping cycles of the balloon pump are accomplished during the period of natural systole. Clearly, in order to provide at least three pumping cycles of the balloon pump within this shortened period, the pumping frequency of the balloon pump must be correspondingly increased. Defining the systolic duty cycle as being the fraction of the total heartbeat period occupied by the systolic period leads to a rule of thumb for the burst mode: that the pumping frequency of the balloon pump must be at least three times the beating frequency of the heat, divided by the systolic duty cycle.

If it is desired to increase perfusion of the coronary arteries in a system used to assist the left heart, one may make a slight modification of the control waveforms as indicated by the dashed lines labelled "C" in FIG. 5. It can be seen that the effect is to omit a deflation of the valve and momentarily to impede outflow from the pump during inflation of the pumping balloon, and application of a pulse of blood pressure to ostia of the coronary arteries, such as the one shown at 19 in FIG. 1. One or more of these events may be used advantageously at the beginning of diastole, as shown for burst mode, or occasionally during continuous mode.

Since pump throughput is essentially proportional to the product of pump displacement and pumping frequency, it follows that higher pumping frequencies permit smaller pumps. At lower pumping frequencies, pump throughput is limited largely by fluid inertia and viscosity forces in the catheter, and is only weakly dependent on pumping displacement up to frequencies at which blood inertia effects become dominant; this leads to a preference for the highest practical pumping frequency. Analysis indicates that a pumping frequency of 1000 strokes per minute is attainable, or almost 14 times the nominal adult heart rate, using helium gas as the drive fluid. It is further likely that arterial compliance effects may be less pronounced at such higher frequencies. For one example, a small pumping balloon of only 7.5 ml displacement, at a pumping frequency of 12 per second and a displacement efficiency of 75% may yield a generous 4 liters per minute.

At higher pumping fequencies, the precise phase relationship between the individual pumping cycles and the cardiac cycle is quite immaterial. Therefore, in the continuous mode, synchronization with the EKG is unnecessary. For this reason, when used bilaterally, this system can support circulation even when the heart is atonic or fibrillating.

It is not absolutely necessary to use an externally-driven valve in order to accomplish pumping. Indeed, some pumping action can be observed if the valve be simply erected by inflation to some moderate constant pressure, especially if a liquid be used as the inflating fluid. A preferable arrangement is to use a one-way passive check valve, several of which have been suggested in the literature. For this purpose, I prefer the structure shown in FIGS. 6, 7 and 8 which are, respectively, a perspective view and sagittal and normal cross-sections of my preferred passive valve. As shown in the Figures, it is an umbrella-like structure comprising inflatable ribs 31 supporting a flexible canopy 30, both made of thin elastomeric material. The structure is mounted upon and cemented to two-lumen catheter 16, and the ribs are fluidically connected to one of the lumens by holes 24, so that they can be erected and collapsed by fluid, preferably a liquid, supplied from the outside through a lumen in the catheter.

Given the foregoing teaching, those skilled in the art to which this invention pertains may readily devise further or extended embodiments. For example, in cases where one or more of the valves of the natural heart are damaged or otherwise incompetent, one may provide the balloon pump with an additional valve at the upstream end, either an externally-driven valve as shown in FIGS. 1 and 3, driven through an additional catheter lumen, or a passive valve as shown in FIGS. 6, 7 and 8. Various other features and advantages not specifically enumerated will occur to those versed in the art, as likewise many variations of the embodiments which have been illustrated, all of which may be achieved without departing from the spirit and scope of the invention as defined by the following claims:

I claim:

1. A high-frequency intra-arterial cardiac support system comprising a balloon pump which may be positioned in a major artery downstream, with respect to the normal blood flow, of a natural heart, said balloon pump comprising a pumping balloon, of small displacement, mounted upon and cyclically inflatable and deflatable by fluid flow through a catheter having a lumen connected fluidically to the pumping balloon and leading to the outside of the body, said balloon pump further comprising a collapsible and erectable valve permitting blood flow in said major artery predominantly in the direction of normal blood flow both when said pumping balloon is inflated and deflated, said valve being composed of thin eleastomeric material and mounted upon said catheter at a position downstream, with respect to normal blood flow, of said pumping balloon and having a generally circular cross section of maximum erected outside diameter just sufficient to substantially occlude said major artery, said system further comprising a control and drive mechanism connected fluidically to said lumen outside of the body providing cyclical fluid flow to said lumen of said catheter for cyclical inflation and deflation of said pumping balloon, said control and drive mechanism comprising drive means for fluidically driving said cyclical flow and said cyclical inflation and deflation of said pumping balloon during both systole and diastole of the natural heart, at a pumping frequency which is at least three times the normal beating frequency of the natural heart; and said small displacement of said pumping balloon being much smaller than the normal stroke volume of the natural heart.

2. For use in a high-frequency intra-arterial cardiac support system, a balloon pump, for positioning in a major artery downstream, with respect to normal blood flow, of a natral heart and comprising, a pumping balloon, an erectable and collapsible balloon valve contiguous to the downstream side of said pumping balloon, a catheter having first and second lumens leading to the outside of the body, and first and second cyclical pumping fluid sources, and fluid source control means, for selectively inflating and deflating said pumping balloon and said balloon valve, both said pumping balloon and said balloon valve being mounted concentrically upon said catheter, said pumping balloon being connected fluidically to said first lumen and adapted to being cyclically inflated and deflated through said first lumen of said catheter by said first cyclical pumping fluid source connected fluidically to said first lumen outside the body, said balloon valve being connected fluidically to said second lumen and adapted to being cyclically inflated and deflated though said second lumen of said catheter by said second cyclical pumping source connected fluidically to said second lumen outside the body, said balloon valve having an erected diameter just sufficient to substantially occlude said major artery to permit blood flow predominantly in the direction of normal blood flow away from said heart when the cyclical phase of said first cyclical pumping fluid source is suitably in advance of the cyclical phase of said second cyclical pumping fluid source, said pumping balloon having an inflated diameter which is less than said erected diameter, said lumens having sufficiently high fluid conductance and said pumping balloon and said balloon valve having sufficiently small displacement that said pumping fluid sources can cyclically inflate and deflate said fluid source control means pumping balloon and said balloon valve at a pumping frequency which is at least three times the normal beat frequency of the natural heart, said fluid source control means being operated to cyclically inflate and deflate both said pumping balloon and said balloon valves at a pumping frequency which is at least three times the normal beating frequency of the natural heart.

3. A balloon pump according to claim 2, for providing support to the left heart and for positioning in the scending aorta between the aortic valve and the ostium of the innominate artery, wherein said pumping balloon is mounted at the end of said catheter and coaxial therewith, said valve is mounted contiguous to said pumping balloon upon said catheter and coaxial therewith, and the total length of said pumping balloon and said valve, parallel to said catheter, is not greater than the distance between said aortic valve and said ostium.

4. A balloon pump according to claim 2, for providing support to the right heart and for positioning in the pulmonary trunk, wherein said valve is mounted upon the end of said catheter and coaxial therewith, said pumping balloon is mounted contiguous to said valve upon said catheter and coaxial therewith, and the total length of said valve and said pumping balloon, parallel to said catheter, is not greater that the length of said pulmonary trunk.

5. A high frequency intra-arterial cardiac support system comprising, a pumping balloon for positioning in a major artery leading from a natural heart and at a location just beyond a natural valve of a natural heart, said pumping balloon having a displacement small compared to the stroke volume of the natural heart, said pumping balloon being mounted upon and cyclically inflatable and deflatable by fluid flow through, a catheter having a lumen connecting fluidically to the pumping balloon and leading to the outside of the body, a collapsible and rectable valve attached to said catheter for positioning in said major artery on the side of said pumping balloon away from said natural valve, said collapsible valve having a generally circular cross section of maximum erected outside diameter just sufficient to substantially occlude said major artery, said collapsible valve permitting blood to flow in said major artery predominantly in the direction away from said natural valve both when said pumping balloon is inflated and deflated, and a control and drive mechanism connected fluidically to said lumen outside of the body and providing cyclical inflation and deflation of said pumping balloon during both disatole and systole of the natural heart at a pumping frequency which is at least three times the normal beating frequency of the natural heart.

6. A high-frequency intra-arterial cardiac support system according to claim 5 operable in burst mode wherein said cyclical inflation and deflation of said pumping balloon occurs mostly during systole of the natural heart, at a pumping frequency which is at least three times the normal beating frequency of the natural heart, divided by the systolic duty cycle, and wherein said control and drive mechanism includes means for operating in a burst mode.

7. A high-frequency intra-arterial cardiac support system according to claim 5 in which said fluid flow to said lumen is a flow of gas.

8. A high-frequency intra-arterial cardiac support system according to claim 5 in which said valve is a collapsible one-way passive check valve oriented to direct blood flow predominantly in the direction of normal blood flow away from the natural heart.

9. A high-frequency intra-arterial cardiac support system according to claim 8 in which said collapsible one-way passive check valve is an umbrella-like structure, of thin elastomeric material, comprising a flexible canopy concentrically mounted to said catheter, concave in the downstream direction, and borne by a plurality of inflatable ribs, said ribs being closed at their outer ends, mounted upon said catheter at their inner ends, and fluidically connected at said inner ends to a further lumen of said cather, said further lumen extending to the outside of the body where a supplied fluid may be introduced to erect said inflatable ribs, or withdrawn to collapse them.

10. A high-frequency intra-arterial cardiac support system according to claim 13 in which said catheter has a further lumen, said valve is a valve balloon connected fluidically to said further lumen and of inflated diameter just sufficient to substantially occlude said major artery and erectable and collapsible by inflation and deflation by fluid flow through said further lumen, and said control and drive mechanism comprises further control means and a further drive means connected fluidically to said further lumen, to provide a further cyclical fluid flow to said further lumen to operate said valve by cyclical inflation and deflation, such that deflation of said pumping balloon takes place when said valve balloon is inflated and said pumping balloon is inflated when said valve balloon is deflated, and at a frequency which is at least three times the normal beating frequency of the natural heart.

11. A high-frequency intra-arterial cardiac support system according to claim 10, wherein said balloon pump is positioned in the ascending aorta, and in which said control and drive mechanism is programmed to omit occasional deflations of said valve.

12. A high-frequency intra-arterial cardiac support system according to claim 11, operable in burst mode with said cyclical fluid flows occurring mostly during systole of the natural heart, in which said control mechanism controls said omitted deflations of said valve to occur near the beginning of diastole of the natural heart, and wherein said control and drive mechanism includes means for operating in a burst mode.

* * * * *

UNITED STATES PATENT AND TRADEMARK OFFICE
CERTIFICATE OF CORRECTION

PATENT NO. : 4,785,795

DATED : November 22, 1988

INVENTOR(S) : Param I. Singh

It is certified that error appears in the above-identified patent and that said Letters Patent is hereby corrected as shown below:

Column 4, line 11, delete "heat" and insert --heart--.

Column 6, line 18, delete "beat" and insert --beating--.

Column 7, line 1, delete "disatole" and insert --distole--.

Column 8, line 4, delete "claim 13" and insert --claim 5--.

Signed and Sealed this

Sixteenth Day of November, 1993

Attest:

BRUCE LEHMAN

Attesting Officer

Commissioner of Patents and Trademarks